United States Patent [19]

Freeman-McRae

[11] Patent Number: Plant 7,219

[45] Date of Patent: Apr. 10, 1990

[54] LILIUM "ETCHINGS"

[75] Inventor: Judith Freeman-McRae, Boring, Oreg.

[73] Assignee: Columbia-Platte Lilies, Inc., Boring, Oreg.

[21] Appl. No.: 286,752

[22] Filed: Dec. 16, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Klarquist, Sparkman, Campbell, Leigh & Whinston

[57] ABSTRACT

A new variety of hybrid lily plant bears large clusters of flowers of excellent form and long persistence, both on the plant and as cut flowers. The flowers of the new plant are particularly characterized by their unusually large and broad-tepalled form, their light cream to white coloring, and by their unusual spotting pattern which consists of several short, narrow "brush-marks" extending from the nectaries. This combination is completely new in the upright Asiatic hybrid lilies. The plant is resistant to disease and shows tolerance of virus. The clone is vigorous and is a good grower and propagator.

1 Drawing Sheet

BACKGROUND OF THE INVENTION

My new variety of lily plant, which I call 'Etchings,' originated as a seedling selected from a group of seedlings growing in a cultivated area at Boring, Oreg. The seedlings resulted from breeding efforts carried on by me since 1981. The breeding efforts had as their objective the production of large-flowered, upfacing lilies in cream and white color tones well suited to forcing for cut flower production out of season, heretofore unknown in the lily breeding art.

I achieved the desired objective by using as the seed parent an upfacing cream-white clone produced from pollinating the clonal cultivar 'Sterling Star' with the clonal cultivar 'Connecticut King.' I used as pollen parent of the new hybrid an upfacing, large-flowered white seedling clone from the cross 'Connecticut Queen'×(Pastel strain, upright white×('Connecticut King'×"brush-marked" seedling)).

The flowers of my new lily are characterized by large size, broad tepals, an upright orientation, and a soft cream to white color pattern accented by a delicate "etched" spotting pattern, unique in this type of lily. In addition, the clone possesses to a high degree desirable characteristics of hybrid vigor, great hardiness, and disease resistance. It possesses all of the desired characteristics of excellence of form, color, and habit. Its large flowers are produced on a single stalk. The clone is vigorous and a good grower and propagator, as observed at Boring, Oreg.

My new variety of lily plant has been asexually reproduced by me and under my direction at Boring, Oreg. Successive generations produced by bulb scale propagation, by natural propagation from bulblets, and by tissue culturing have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the connection of the flower to the stem, and in particular the novel and distinctive large, pale cream to white flowers with their unusual lightly "etched" spotting pattern.

DESCRIPTION OF THE NEW VARIETY

The following is a detailed description of my new variety of Asiatic hybrid lily, with nomenclature according to the *International Lily Register* (The Royal Horticultural Society of London, Second Edition, 1969), and with color designations according to the Colour Chart of The Royal Horticultural Society, published by the Society in 1966.

Plant

Origin: Seedling.

Seed parent: Lilium 'Sterling Star' (unpatented)×'Connecticut King.'

Pollen parent: Lilium 'Connecticut Queen' (unpatented)×(Pastel hybrid, white upfacing clone×('Connecticut King'×"brush-marked" seedling)).

Commercial classification: Hybrid Lilium clone.

Horticultural classification: Division 1-A, upright Asiatic hybrid lily, according to the Horticultural Classification of Lilies, The Royal Horticultural Society of London.

Form: Single stem, erect and stately.

Height: Bulbs in their second year of growth after scale propagation in the field produce stems averaging 75 to 90 cm tall.

Growth: Vigorous and upright.

Foliage quantity: Abundant.

Size of leaf: 8 to 12 cm long×1 to 2 cm wide.

Shape of leaf: Lanceolate (pointed).

Texture: Leathery and glossy.

Color: Medium green, lighter on lower side.

Bulb size: Any size, ranging to 25 cm circumference commercially.

Bulb color: White.

The Bud

Form: Obtuse, ovoid, and long.

Size: 8 to 9 cm long and 5–6 cm in circumference just prior to opening.

Opening: Bud opens slowly, in response to morning light; this takes about one hour.

Color: Palest cream to white just prior to opening and as tepals unfurl.

Peduncle: Averages 2 to 5 cm, but it may elongate if light levels are too low or if bulbs have been improperly stored prior to forcing. Color is medium green; if grown at very cool temperatures, green color may be deepened by a light plum overlay.

The Flower

Blooming habit: Annually in midseason; flowers once and profusely.

Size: Large flowers are 15 to 19 cm in diameter; the outer tepals are 2.5 to 3 cm wide, and the inner tepals are 3.0 to 3.5 cm wide.

Borne: In a single racemic inflorescence producing 6 to 8 buds (from a bulb 12 to 15 cm in circumference). Inflorescence averages 20–25 cm long.

Shape: First open in cup shape, which flattens as tepals recurve by second day.

Tepalage: Typical of genus Lilium, with 6 imbricated tepals.

Tepal color: Flowers are distinguished by their unusual color pattern which contrasts the flower with delicate magenta "etchings." The base color is an extremely pale cream The Royal Horticultural Society Colour Code 9D (R.H.S. CC 9D) under conditions of low light or low temperatures when the flowers first open, fading to pure white by the second day. With adequate light conditions, the flowers are pure white when they open. The border of the nectary furrows is lightly pubescent and white.

Tepal spotting: The basal third of each tepal is marked with 2 to 4 small and narrow "brush-marks" averaging 1–3 mm wide and 1–2 cm long, extending from the nectaries. These "brush-marks" create a unique "etched" spotting pattern. Each tepal also carries 10–20 very small magenta papillae at its extreme base, parallel to the nectaries. The "etches" and the papillae are the same shade of magenta, (R.H.S. CC Red-Purple 71A-B). This color will become slightly more purple as the flower ages; it may be slightly redder under high light intensity.

Tepal longevity: Tepals stay on stems about three weeks.

Pedicel length: Average 8 to 10 cm long.

Pedicel color: Medium green.

Pedicel form: Sturdy and ascending at an angle of 45 to 60 degrees from the horizontal. Very rarely has secondary buds.

Color changes: The flower lightens to pure white coloration shortly after opening, if light levels are adequate for cut flower maintenance. (If temperature is warm enough and light levels are adequate, it will be pure white at the time of opening; low light levels and cool temperature retard the whitening of the flower.)

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut flower.

Reproductive Organs

Stamens: Arrangement typical of genus Lilium. Six stamens with soft cream (R.H.S. CC 9D) to white filaments 5 cm long.

Pollen and anthers (dehisced): Greyed orange (R.H.S. CC 172A).

Pistil: One in number, 5 cm long.

Stigma: Soft green with light plum overlay.

Characteristics of ovary: Characteristic of genus Lilium.

Fruit

Fertility: Bears viable seed.

Shape: Ovoid.

Color at maturity: Soft brown, sometimes overlaid with soft plum.

My new variety most closely resembles 'Mt. Blanc' but it has flowers of greater size and thickness and is distinguished by its unusual "etched" spotting pattern. At first opening, the flower color of my new variety is pale cream to true white, not the deep cream of 'Mt. Blanc'. The stems of my new variety are longer, and its flowers, with their broader tepals and greater thickness, are longer lasting than those of 'Mt. Blanc.'

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form; and in particular by its exceptionally large and broad-tepalled flowers of pale cream to pure white enriched by delicate "etched" spotting at the tepal base, a color pattern and form unique among Asiatic hydrid lilies suited to forcing and to mass commercial cultivation.

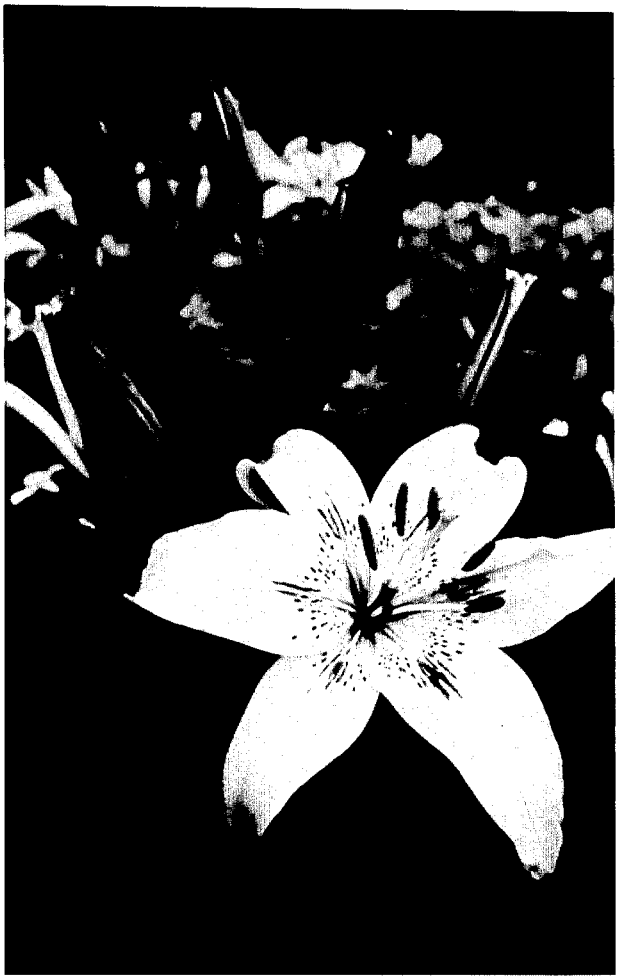

* * * * *